United States Patent [19]

Visser et al.

[11] Patent Number: 5,281,313

[45] Date of Patent: Jan. 25, 1994

[54] SELECTIVE COMBUSTIBLE SENSOR AND METHOD

[75] Inventors: Jacobus H. Visser, Belleville; Eleftherios M. Logothetis, Birmingham; Lajos Rimai, Dearborn; Richard E. Soltis, Redford Township, Redford County, all of Mich.

[73] Assignee: Ford Motor Company, Dearborn, Mich.

[21] Appl. No.: 33,732

[22] Filed: Mar. 18, 1993

[51] Int. Cl.$^5$ ............................................ G01N 27/26
[52] U.S. Cl. ............................ 204/153.1; 204/153.14; 204/153.16; 204/425
[58] Field of Search ................ 204/425, 153.1, 153.14, 204/153.16, 426, 427

[56] References Cited

U.S. PATENT DOCUMENTS

| | | | |
|---|---|---|---|
| 4,272,329 | 6/1981 | Hetrick et al. | 204/425 |
| 4,272,330 | 6/1981 | Hetrick | 204/425 |
| 4,272,331 | 6/1981 | Hetrick | 204/425 |
| 4,841,934 | 6/1989 | Logothetis et al. | 204/406 |
| 4,851,103 | 7/1989 | Usami et al. | 204/425 |
| 5,080,765 | 1/1992 | Wang et al. | 204/425 |
| 5,089,113 | 2/1992 | Logothetis et al. | 204/425 |
| 5,145,566 | 9/1992 | Logothetis et al. | 204/425 |

FOREIGN PATENT DOCUMENTS

0361692 8/1989 European Pat. Off. .

OTHER PUBLICATIONS

"Chemical and Physical Sensors Based On Oxygen Pumping With Solid-State Electrochemical Cells", by E. M. Logothetis, J. H. Visser, R. E. Soltis and L. Rimai; Dated: Apr. 30, 1992; pp. 183-189.
"Sensors For Measuring Combustibles In The Absence Of Oxygen", by J. H. Visser, R. E. Soltis, L. Rimai and E. M. Logothetis; Dated: May 19, 1992; pp. 233-239.
"Air-to-Fuel Sensors Based On Oxygen Pumping", by E. M. Logothetis; Dated: Sep. 10, 1987; pp. 1058-1073.
"A High-Sensitivity Sensor For The Measurement Of Combustible Gas Mixtures", by: E. M. Logothetis, W. C. Vassel, R. E. Hetrick and W. J. Kaiser; Dated: Jun. 1985; pp. 363-372.
"Gas-Diffusion-Controlled Solid-Electrolyte Oxygen Sensors", by Hermann Dietz; Dated: Sep. 11, 1981; pp. 175-183.

*Primary Examiner*—John Niebling
*Assistant Examiner*—Bruce F. Bell
*Attorney, Agent, or Firm*—Lorraine S. Melotik; Roger L. May

[57] ABSTRACT

A method of operating a selective combustible sensor having a pump cell and a sensor cell includes the steps of immersing the sensor in a gaseous atmosphere having at least two combustible gases and oxygen gas and allowing the gaseous atmosphere to enter a region between the pump cell and the sensor cell, applying a pumping current to the pump cell, sensing an e.m.f. ($V_s$), across the sensor cell, varying at least either the $V_s$ or temperature to make the sensor insensitive to one of the combustible gases, and detecting the other combustible gases present in the gaseous atmosphere.

17 Claims, 3 Drawing Sheets

SELECTIVE COMBUSTIBLE SENSOR AND METHOD

BACKGROUND OF THE INVENTION

1. Field of the Invention

The present invention relates generally to combustible sensors and, more particularly, to a selective combustible sensor and method for measuring the concentration of combustibles in a gaseous atmosphere.

2. Description of the Related Art

Solid-state electrochemical cells based on oxygen-ion conducting zirconium dioxide ($ZrO_2$) have found extensive use as oxygen sensors in many applications. One of these is in the automotive vehicle industry, where the oxygen sensor is used to control the air-to-fuel (A/F) ratio of an engine by measuring oxygen partial pressure in engine exhaust. Typical automotive oxygen sensors consist of a single $ZrO_2$ cell operated in an open-circuit mode (Nernst cell) and are used for stoichiometric A/F ratio control. Oxygen sensors more sensitive than the Nernst cell are based on the oxygen-pumping principle, i.e., the application of an external current to transfer (pump) oxygen from a negative potential side to a positive potential side of the $ZrO_2$ cell. Automotive oxygen sensors of this type are designed for operation with lean A/F ratio mixtures. These sensors are commonly called lean exhaust gas oxygen, LEGO, sensors.

Examples of such LEGO sensors are disclosed in U.S. Pat. Nos. 4,272,329, 4,272,330 and 4,272,331 to Hetrick et al. and assigned to the same assignee as the present invention. These patented LEGO sensors, which are immersed in a gaseous atmosphere, are constructed to define an enclosed volume which communicates with the atmosphere by way of a small aperture. The above-referenced patented LEGO sensors include two electrochemical cells which define the enclosed volume. One cell is called the pump cell while the other cell is called the sensor cell. When attached to an external power supply, a current (Ip) through the pump cell either adds or removes (from or to the atmosphere) gaseous oxygen from the enclosed volume. As a result of the pumping action, an electromotive force or e.m.f. ($V_s$) develops across the sensor cell which can be used to measure the change in oxygen partial pressure in the enclosed volume relative to the atmosphere.

Although the above LEGO sensors have worked well, they have been used at constant temperature and $V_s$. As a result, these sensors have not been used to selectively detect combustible gases in a gaseous atmosphere. Also, these sensors have not been used to detect one combustible gas in the presence of other combustible gases in a gaseous atmosphere.

SUMMARY OF THE INVENTION

Accordingly, the present invention is a method of operating a selective combustible sensor, the sensor having a pump cell and a sensor cell. The method includes the steps of immersing the sensor in a gaseous atmosphere having at least two combustible gases and oxygen gas and allowing the gaseous atmosphere to enter a region between the pump cell and the sensor cell, applying a pumping current to the pump cell, and sensing an e.m.f. ($V_s$) across the sensor cell. The method also includes the steps of varying at least either the $V_s$ or temperature of the sensor to make the sensor insensitive to one of the combustible gases, and detecting the other combustible gases present in the gaseous atmosphere.

One feature of the present invention is that a selective combustible sensor is used for detecting and measuring the concentration of combustible gases in a gaseous atmosphere. Another feature of the present invention is that a method is provided for operating a LEGO sensor to measure the concentration of combustible gases in a gaseous atmosphere. Yet another feature of the present invention is that a method is provided for operating a selective combustible sensor for detecting one combustible gas in the presence of other combustible gases in a gaseous atmosphere. Still another feature of the present invention is that a method is provided for operating a selective combustible sensor that provides control of sensitivity and selectivity. A further feature of the present invention is that the selectivity and sensitivity of the sensor are based on the differences in diffusivity between the various combustibles in a gaseous atmosphere relative to the diffusivity of oxygen in the gaseous atmosphere. A still further feature of the present invention is that the selective combustible sensor has a fast response time and low cost compared to conventional combustible sensors.

Other objects, features and advantages of the present invention will be readily appreciated as the same becomes better understood after reading the subsequent description taken in conjunction with the accompanying drawings.

DESCRIPTION OF THE PREFERRED EMBODIMENT(S)

Figure 1:
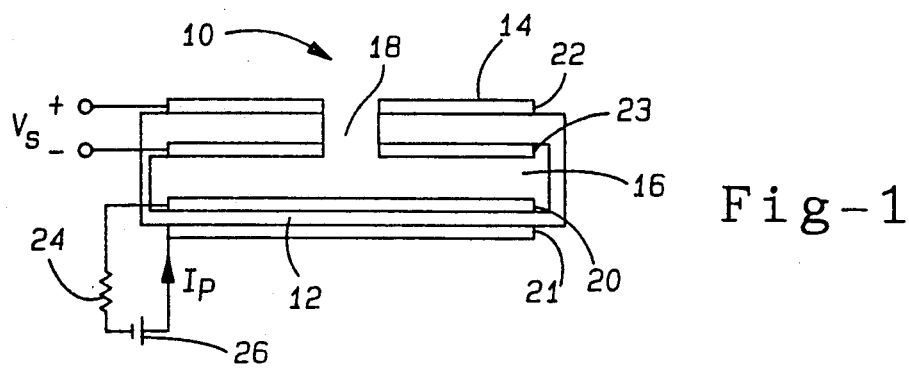
FIG. 1 is a schematic, partly cross-section diagram, of a selective combustible sensor according to the present invention.

Referring to FIG. 1, a selective combustible sensor or device 10, according to the present invention, is illustrated. The sensor 10 is of the LEGO type used to control the air-to-fuel (A/F) ratio of an engine (not shown). Such a LEGO sensor is described in U.S. Pat. No. 4,272,329 to Hetrick et al., the disclosure of which is hereby incorporated by reference. It should be appreciated that the sensor 10 may include a heater (not shown), for example, and a feedback circuit (not shown). It should also be appreciated that the sensor 10 is immersed in an ambient gaseous atmosphere and may be located on an automotive vehicle (not shown), for example, in the passenger compartment thereof.

The sensor 10 includes a pump cell 12 and a sensor cell 14 both adjacent to a cavity 16 which is in communication with the atmosphere through a small diameter aperture 18. The cells 12 and 14 are of the yttria ($Y_2O_3$) doped zirconium dioxide ($ZrO_2$) type and have porous catalytic (e.g., platinum) electrodes 20,21 and 22,23 respectively. It should be appreciated that the sensor 10 is not illustrated to scale and that the thickness of the electrodes 20,21 and 22,23 is much smaller than the thickness of the $ZrO_2$ material of the cells 12 and 14.

In operation, pump cell current, $I_p$, is applied to the pump cell 12 through a resistor 24 by means of a power supply 26. A sensed voltage, $V_s$, across the sensor cell 14 may be applied to an input of a comparator (not shown) for the feedback circuit. It should be appreciated that the feedback circuit is conventional and known in the art.

The principle of operation of the sensor 10 will now be described. When two sides of an electrochemical cell are exposed to different oxygen partial pressures, $P_1$ and $P_2$ at elevated temperatures (e.g., T>300° C.), an open-circuit e.m.f. develops across the cell given by the Nernst equation:

$$\text{e.m.f.}(V_s) = (kT/(4e)) \ln(P_2/P_1)$$

In this equation, k is the Boltzmann constant, e is the electron charge, and T is the absolute temperature. If the partial pressure on one side of the cell is known, the partial pressure on the other side of the cell can be determined from the measurement of the e.m.f. A further discussion of these principles may be found in a publication, "Chemical And Physical Sensors Based On Oxygen Pumping With Solid-State Electrochemical Cells", Sensors and Actuators, B, 9, pgs. 183-189 (1992), which is hereby incorporated by reference.

For example, the sensor 10 can be used for measuring the concentration of oxygen ($O_2$) in a gaseous atmosphere such as air ($O_2/N_2$ mixture). When the electrode 20 of the pump cell 12 is negatively biased with respect to the electrode 21, the pumping current $I_p$ removes $O_2$ molecules out of the cavity 16 at a rate of $I_p/(4e)$. This oxygen transfer will cause the oxygen partial pressure inside the cavity 16 to decrease from an initial value $P_2$ to a lower value $P_1$. Because of the difference in oxygen partial pressures inside and outside the cavity 16, an emf ($V_s$) equal to $(kT/(4e)) \ln (P_2/P_1)$ develops across the sensor cell 14 and a diffusional flux of $O_2$ equal to $B(D_{O2}/(kT)) (P_2-P_1)$ is established from the atmosphere into the cavity 16 through the aperture 18. In the above expression, $D_{O2}$ is the diffusion constant of $O_2$ and B is a constant that depends on the geometrical characteristics of the aperture 18. It should be appreciated that in the case of bulk diffusion through a single straight round (e.g., cylindrical) pore or aperture, B is proportional to S/L, where S is the area and L is the length of the pore or aperture.

Under steady-state conditions, the rate at which $O_2$ is pumped out of the cavity 16 by the pumping current $I_p$ is equal to the diffusional flux of $O_2$ (in molecules per second) into the cavity 16 as follows:

$$I_p/(4e) = B(D_{O2}/(kT)) (P_2-P_1)$$

Combining this equation with that for $V_s$, the resulting equation is:

$$I_p = 4eB(D_{O2}/(kT))[1-\exp(-4e\,V_s/(kT))]P_2$$

As the pumping voltage and current increase, the oxygen partial pressure $P_1$ inside the cavity 16 decreases and $V_s$ increases. If the pumping current ($I_p$) is controlled so that $V_s$ always has a prescribed value, $I_p$ becomes proportional to $P_2$.

According to the present invention, the sensor 10 can be used for measuring the concentration of combustible gases (hydrocarbons, alcohols, $H_2$, CO, etc.) in an ambient gaseous atmosphere such as air based on the determination of left-over oxygen after oxidation of the combustibles. For clarity, the operation of the sensor 10 will be described for one combustible (comb) present in dry (laboratory) air which has a constant oxygen concentration of 20.9%. It should be appreciated that the method of operating the sensor 10 to measure a combustible in a gaseous atmosphere is not limited to measuring a combustible in air. For example, a combustible can be detected in any gaseous atmosphere where sufficient oxygen is present to oxidize all combustible gas molecules at the catalytic electrodes of the sensor 10.

For the sensor 10 of FIG. 1, $P_{O2}$ and $P_{comb}$ are the partial pressures of oxygen and the combustible in the air surrounding the sensor 10. When the sensor 10 is heated by the heater (not shown) to a temperature in the range of 550°-850° C., combustible gas molecules react with oxygen gas molecules on the electrodes 20,21 and 22,23 of the cells 12 and 14, respectively, to form $CO_2$ and/or $H_2O$. The decrease in $P_{O2}$ and $P_{comb}$ inside the cavity 16 gives rise to diffusional fluxes of the oxygen and combustible gas molecules from the ambient gaseous atmosphere into the cavity 16 through the aperture 18. In addition, a voltage from the power supply 26 can be applied across the pump cell 12, which results in a pumping current ($I_p$) which pumps some $O_2$ in or out of the cavity 16 and causes an increase or decrease in the oxygen partial pressure therein. If $P_{O2in}$ is the oxygen partial pressure inside the cavity 16, an e.m.f. ($V_s$), develops across the sensor cell 14 given by the following Nernst equation:

$$V_s = (kT/(4e)) \ln (P_{O2out}/P_{O2in})$$

where $P_{O2out}$ is the oxygen partial pressure at the electrode 22 outside of the cavity 16. Assuming thermodynamic equilibrium at the electrode 22, and the following equation results:

$$P_{O2out} = P_{O2} - nP_{comb}$$

where n is the number of oxygen gas molecules required to oxidize one of the combustible gas molecules. Assuming that all combustible gas molecules are completely reacted inside the cavity 16, the diffusional fluxes of oxygen and the combustible (in molecules per second) are:

$$F(O_2) = B(D_{O2}/(kT)) (P_{O2}-P_{O2in})$$

$$F(\text{comb}) = B(D_{comb}/(kT)) P_{comb}$$

where B is again a constant determined by the geometrical characteristics of the aperture 18 and $D_{O2}$ and $D_{comb}$ are the diffusion constants for the oxygen and combustible, respectively. Because one gas molecule of the combustible reacts with n gas molecules of oxygen, the following relation is obtained for steady-state conditions:

$$F(O_2) = nF(\text{comb}) - I_p/(4e)$$

where $I_p/(4e)$ is the rate by which oxygen is pumped out of the cavity 16 by the pumping current $I_p$.

Combining the above equations, the following equation for the pumping current $I_p$ is obtained:

$$I_p = 4eB(D_{O2}/(kT))[\{1-exp(-4eV_s/(kT))\}P_{O2} - n \cdot P_{comb}\{D_{comb}/D_{O2}-exp(-4eV_s/(kT))\}]$$

If the pumping current is controlled so that $V_s$ is maintained at a prescribed value, $I_p$ is related to the partial pressure of the combustible in air. In terms of the concentrations (in volume percentage) of oxygen ($C_{O2}$) and the combustible ($C_{comb}$), the equation above for the pumping current $I_p$ can be rewritten as:

$$I_p = 4eB(D_{O2}/(kT))[\{1-exp(-4eV_s/(kT))\}C_{O2} - n \cdot C_{comb}\{D_{comb}/D_{O2}-exp(-4eV_s/(kT))\}]P_T$$

where $P_T$ is the total gas pressure.

If the reaction of the combustible with oxygen inside the cavity 16 is not complete or if thermodynamic equilibrium is not established at the electrodes 22 and 23 of the sensor cell 14, a more complex relation exists between the pumping current $I_p$ and the combustible partial pressure $P_{comb}$. If this more complex relation is unknown, the sensor 10 can be calibrated and used. Also, diffusion effects at the electrodes 22 and 23 which have been neglected, result in a more complex relation for the pumping current $I_p$. If the sensor 10 is operated or constructed such that diffusion effects can not be neglected, the electrodes 22 and 23 may include different diffusion barriers (not shown), for example, one with large pores or apertures where ordinary (bulk) diffusion is the dominant diffusion process or one with small pores or apertures where Knudsen diffusion is the dominant diffusion process. A further discussion of these diffusion processes may be found in a publication, "Gas-diffusion-controlled solid-electrolyte oxygen sensors" by H. Dietz, Solid State Ionics 6, pgs. 175-183 (1982).

If the diameter of aperture 18 is much smaller than a mean free path of the gas molecules in the gaseous atmosphere, the diffusion process is dominated by Knudsen diffusion. This diffusion coefficient is independent of absolute pressure. As a consequence, the equation for the pumping current $I_p$ will result in a pumping current $I_p$ that linearly depends on the absolute pressure of the gaseous atmosphere.

If the diameter of aperture 18 is much larger than the mean free path of the gas molecules in the gaseous atmosphere, the diffusion process is dominated by ordinary (bulk) diffusion. The diffusion coefficients $D_{O2}$ and $D_{comb}$ are (in good approximation) binary diffusion coefficients of $O_2$ in $N_2$ and combustible in $N_2$, respectively. These binary diffusion coefficients are inversely proportional to the absolute pressure. As a consequence, the equation for the pumping current $I_p$ will result in a pumping current $I_p$ independent of absolute pressure. Therefore, the equation for the pumping current $I_p$ can then be rewritten as:

$$I_p = 4eAD_{O2}[\{1-exp(-4eV_s/(kT))\}C_{O2} - nC_{comb}\{D_{comb}/D_{O2}-exp(-4eV_s/(kT))\}]$$

where A is a constant determined by the geometrical characteristics of the aperture 18.

If the diameter of aperture 18 is comparable with the mean free path of the gas molecules, both types of diffusion processes are involved. It should be appreciated that the cavity 16 and the single aperture 18 of the sensor 10 can be in the form of a porous layer (not shown) that acts as a diffusion barrier, as described in a publication, "Air-to-Fuel Sensors Based on Oxygen Pumping" by E. M. Logothetis, Ceramic Engineering and Science Proceedings, Vol. 8, Sept.-Oct. 1987.

For a combustible gas in air, $C_{O2}$ is not constant (e.g., equal to 20.9%), but depends on the concentration of the combustible gas in (dry) air as follows:

$$C_{O2} = 20.9 (1-C_{comb}/100)\%$$

Figure 2:
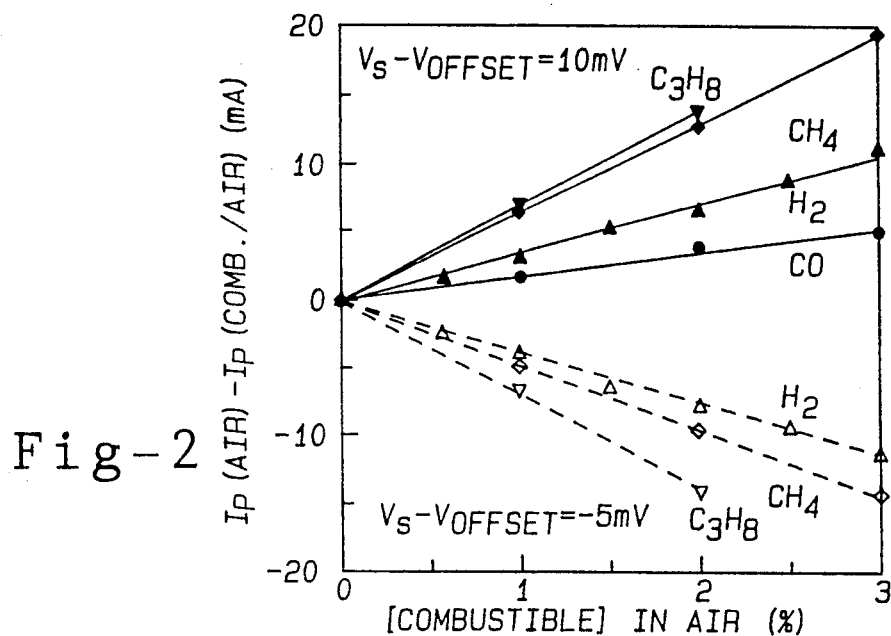
FIG. 2 is a graph of an experimentally measured change in pumping current ($I_p$) versus concentration of several combustibles in air for the sensor of FIG. 1.

A good measure for the sensitivity of the sensor 10 is the change in pumping current $I_p$ as the concentration of combustible in the gaseous atmosphere increases, i.e. a differential pumping current $I_p(air) - I_p(comb.\ in\ air)$. As illustrated in FIG. 2, a graph of an experimentally measured differential pumping current for the sensor 10 is shown. For a constant $V_s$, the change in pumping current is linear to the concentration of the combustible for various combustible gases in air. As illustrated, the sensor 10 had a non-zero voltage (V) offset when no pumping current was applied and the measurements were corrected for this voltage offset. The sensor 10 is able to detect combustibles below the Lower Explosive Limit (e.g., 1.0 to 5.0% in air) for most combustible gases. It should be appreciated that the response time of the sensor 10 was measured to be less than 200 milliseconds (ms), which is substantially faster than the response times (2-20 seconds) for conventional (calorimetric/pellistor and resistive type) combustible sensors.

Referring to FIG. 2, for one value of $V_s$, the sensitivity of the sensor 10 to methane ($CH_4$) is approximately equal to that for propane ($C_3H_8$), while for another value of $V_s$, the sensitivity of the sensor 10 to methane ($CH_4$) is closer to that of hydrogen ($H_2$). Examination of the above equations for the pumping current $I_p$ reveals that for every combustible with a diffusion coefficient $D_{comb}$, there is a value of $V_s/T$ for which $D_{comb}/D_{O2}-exp(-4eV_s/(kT))$ equals zero, i.e., the sensor 10 is insensitive to the combustible for that particular value of $V_s/T$.

According to the present invention, the sensor 10 can be used to distinguish between a plurality of combustible gases. With no combustible gas present and $V_s=0$, the pumping current $I_p$ will be zero. When a combustible gas is present, the temperature is kept constant, and $V_s$ is kept zero, the value and sign of the pumping current $I_p$ depends on $D_{comb}/D_{O2}$ e.g., $$D_{comb}/D_{O2} > 1 \quad I_p < 0$$

$$D_{comb}/D_{O2} = 1 \quad I_p = 0$$

$$D_{comb}/D_{O2} < 1 \quad I_p > 0$$

Figure 3:
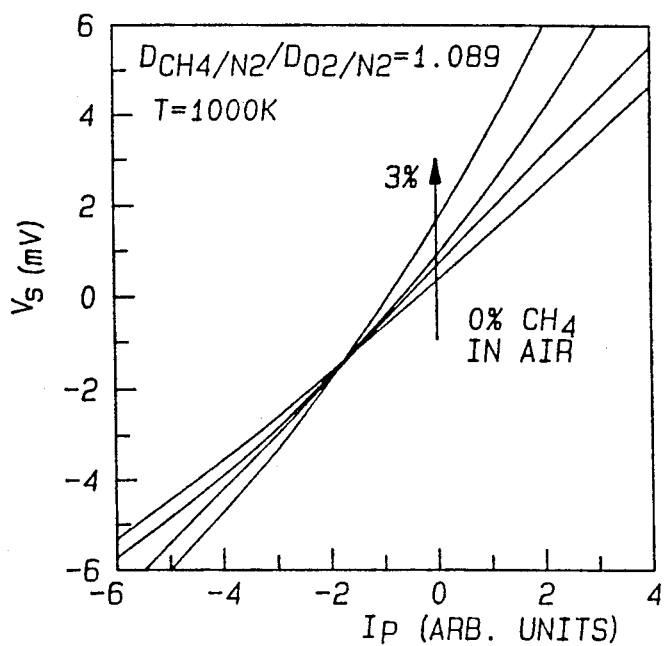
FIG. 3 is a graph of electromotive force ($V_s$) versus pumping current ($I_p$) for a combustible (methane) at several concentrations in air for the sensor of FIG. 1.
Figure 4:
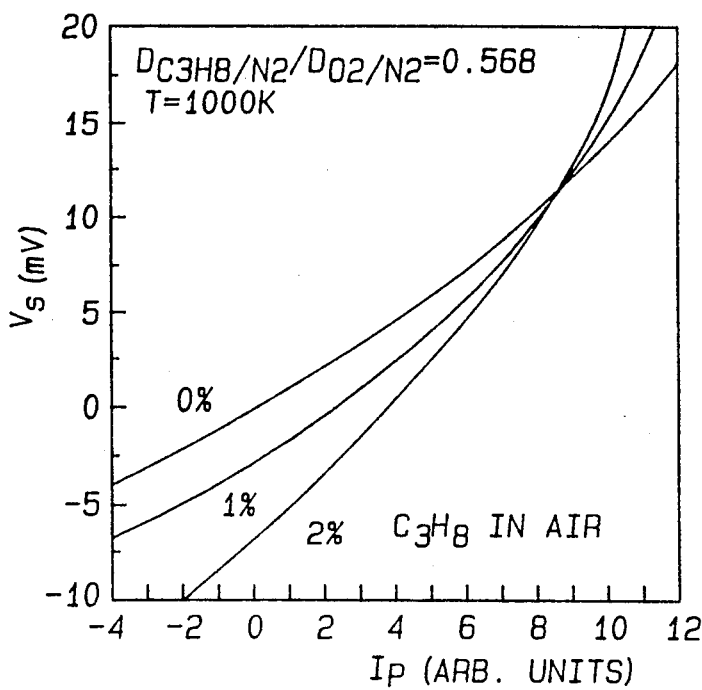
FIG. 4 is a graph of $V_s$ versus $I_p$ for another combustible (propane) at several concentrations in air for the sensor of FIG. 1

If $D_{comb}/D_{O2} > 1$, the combustible diffuses more rapidly than oxygen. Inside the cavity 16, the combustible oxidizes to $CO_2$ and/or $H_2O$, thus reducing the concentration of the combustible and oxygen. Since the combustible diffuses into the cavity 16 more rapidly, the oxygen concentration inside the cavity 16 will be lower than that on the outside of the electrode 22 for the sensor cell 14. As a result, $I_p < 0$ milliamps (mA) and pumping additional oxygen into cavity 16 is required to keep $V_s=0$ millivolts (mV). For $D_{comb}/D_{O2} < 1$, $I_p > 0$ mA and oxygen needs to be pumped out of the cavity 16, because a higher oxygen concentration in the cavity 16 than on the outside of the electrode 22 will exist. For example, the results for methane ($CH_4$) in air and propane ($C_3H_8$) in air in the case of ordinary (bulk) diffusion, are illustrated in FIGS. 3 and 4, respectively. It should be appreciated that the temperature T is kept constant at 1000 K. It should also be appreciated that $V_s$ is in units of millivolts (mV) and $I_p$ is in arbitrary units.

Referring to FIGS. 3 and 4, to have the sensor 10 selective to $CH_4$ for a $CH_4/C_3H_8$ mixture in air, the sensor 10 is operated at approximately $V_s=12$ mV. At $V_s=12$ mV, the sensor 10 does not respond to any concentration of $C_3H_8$, i.e. the required pumping current $I_p$ to obtain $V_s=12$ mV is identical to the pumping current $I_p$ required for air (FIG. 4). However, the sensor 10 does respond to $CH_4$ (FIG. 3). Therefore, at $V_s=12$ mV, the pumping current $I_p$ is measured for the sensor 10 and the concentration of $CH_4$ is calculated according to the above-described pumping current equation. It should be appreciated that the sensor 10 can be selective to $C_3H_8$ by operating the sensor 10 at approximately $V_s=-2$ mV. It should also be appreciated that making the sensor 10 insensitive to a particular combustible can be accomplished by changing both $V_s$ and the temperature T. It should further be appreciated that to ensure proper operation of the $ZrO_2$ material and to establish thermodynamic equilibrium at the electrodes 20,21 and 22,23, the temperature must be kept within a predetermined temperature range (e.g. 550°-850° C.). It should still further be appreciated that the diffusion coefficients are dependent on temperature.

Figure 5:
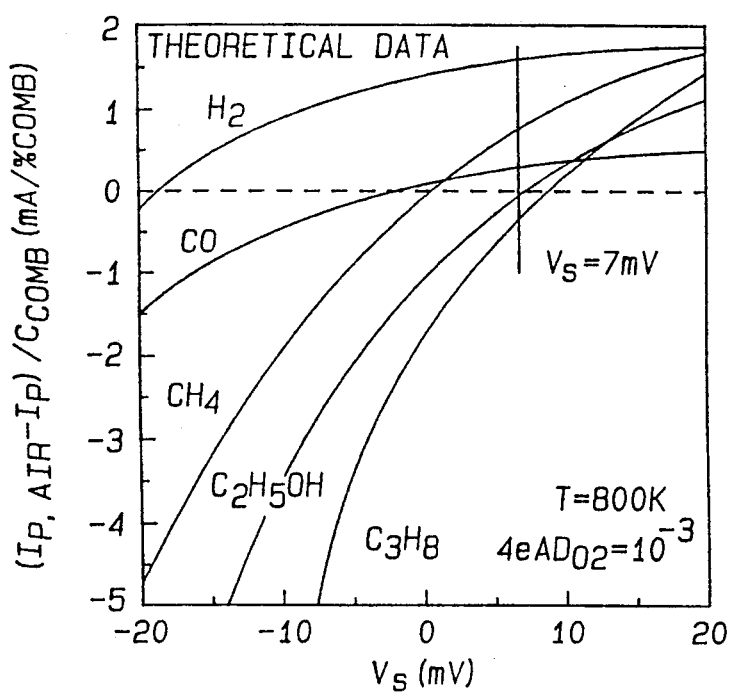
FIG. 5 is a graph of a change in $I_p$ per percent combustible versus $V_s$ for several combustible gases in air for the sensor of FIG. 1.

As another example, to detect $CH_4$ in a $CH_4/C_2H_5OH$ mixture in air, the sensor 10 is operated at $V_s=7.0$ mV as illustrated in FIG. 5. As illustrated, any concentration of $C_2H_5OH$ will cause a zero change in pumping current at $V_s=7.0$ mV and $CH_4$ will cause a change in pumping current of approximately 1.0 mA per percent $CH_4$. Thus, $CH_4$ can be measured with total selectivity in the presence of $C_2H_5OH$ when the sensor 10 is operated at $V_s=7.0$ mV.

Figure 6:
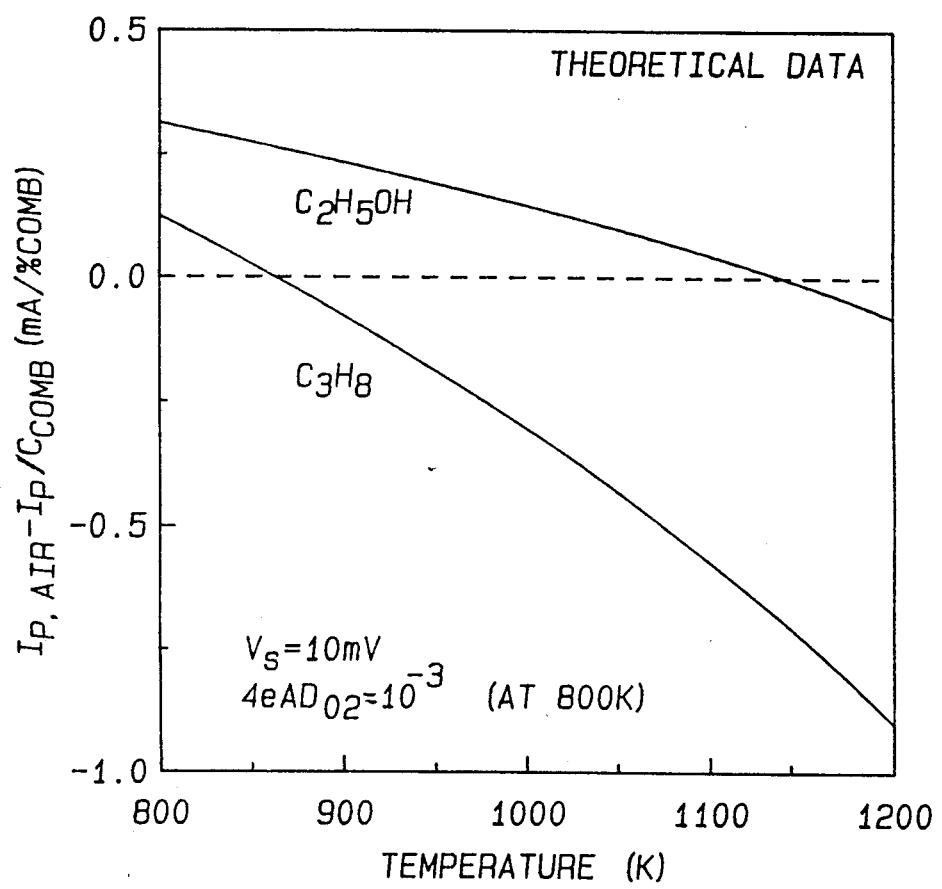
FIG. 6 is a graph of a change in $I_p$ per percent combustible versus temperature for two combustible gases in air for the sensor of FIG. 1.

Referring to FIG. 6, a change in pumping current $I_p$ with respect to the pumping current $I_p$ in air per percent combustible in air for propane ($C_3H_8$) in air, and ethanol ($C_2H_5OH$) in air is shown as a function of the temperature of the sensor 10 when $V_s$ is controlled or held constant at 10 mV. Around 600° C., the sensor 10 is insensitive to propane; while at around 850° C., the sensor 10 is insensitive to ethanol. In this calculation, ordinary (bulk) diffusion was assumed to be the dominant diffusion mechanism through the aperture 18. It should be appreciated that the temperature of the sensor 10 may be varied by a heater (not shown).

As described above, to selectively detect several combustibles, the output or pumping current $I_p$ of the sensor 10 must be measured at various $V_s$. This can be accomplished by using a single sensor 10 operated sequentially at various $V_s$ or using an array of sensors 10 with each sensor operated at a different $V_s$. It should be appreciated that a neural network (not shown) may be used to calculate a large number of concentrations.

When the measurements are performed in a gaseous atmosphere with an unknown (but sufficient) oxygen concentration, a measurement of the pumping current $I_p$ at another $V_s$ must be carried out (for example, at $V_s=0$ mV). This additional measurement is required to determine the unknown oxygen concentration. It should be appreciated that the necessity of doing this additional measurement would be due to an unknown oxygen concentration in air caused by large changes in relative humidity.

For a mixture of combustibles in air, the pumping current equation can be generalized to:

$$I_p = 4eAD_{O2}\{[1 - exp(-4eV_s/(kT))]C_{O2} - \Sigma_i\{n_iC_{combi}[D_{combi}/D_{O2} - exp(-4eV_s/(kT))]\}\}$$

$$C_{O2} = 20.9(1 - \Sigma_i\{C_{combi}/100\})\%$$

It should be appreciated that it is assumed that the oxidation of various combustibles takes place independent of the presence of another combustible. It should also be appreciated that it is assumed that enough oxygen is present for complete reaction of the combustibles.

Accordingly, the sensor 10 can be operated to measure binary mixtures of known combustible gases in air by operating the sensor 10 at one $V_s$ or temperature in order to make it selective or insensitive to one of the combustible gases. For mixtures of a number of known combustible gases and/or unknown $O_2$ concentration, the sensor 10 can be operated for a range of $V_s$ and then made successively insensitive to each of the combustibles by operating at appropriate values of $V_s$. For mixtures of a number of unknown combustible gases, $V_s$ must be varied over a wide range of values and a neural network can be used to evaluate the measurement data. It should be appreciated that the range of $V_s$ is not necessarily a discrete number of values and that $V_s$ could be changed in an analog manner and the resulting analog pumping current signal then be fed to the neural network.

The present invention has been described in an illustrative manner. It is to be understood that the terminology which has been used is intended to be in the nature of words of description rather than of limitation.

Many modifications and variations of the present invention are possible in light of the above teachings. Therefore, within the scope of the appended claims, the present invention may be practiced otherwise than as specifically described.

What is claimed is:

1. A method of operating a selective combustible sensor, the sensor having a pump cell and a sensor cell, said method comprising the steps of:
   immersing the sensor in a gaseous atmosphere having at least two combustible gases and oxygen gas and allowing the atmosphere to enter a region between the pump cell and the sensor cell;
   applying a pumping current to the pump cell;
   sensing an electromotive force ($V_s$) across the sensor cell;
   varying at least either the $V_s$ or temperature of the sensor to make the sensor insensitive to one of the combustible gases; and
   detecting the other combustible gases present in the gaseous atmosphere.

2. A method as set forth in claim 1 including the step of determining a $V_s$ for a zero change in pumping current with respect to a pumping current when no combustible is present for each combustible gas prior to said step of varying.

3. A method as set forth in claim 2 wherein said step of determining comprises either one of calculating or calibrating the sensor for the zero change of each combustible gas.

4. A method as set forth in claim 1 wherein said step of varying comprises adjusting the pumping current such that the sensor cell has a $V_s$ that corresponds to a zero differential pumping current for one of the combustible gases.

5. A method as set forth in claim 1 wherein said step of varying comprises adjusting the temperature of the sensor such that the sensor has a temperature that corresponds to a zero differential pumping current for one of the combustible gases.

6. A method as set forth in claim 1 wherein said step of detecting comprises measuring a pumping current of the pump cell, and calculating the concentration of various combustible gases from the measured values of the pumping current.

7. A method as set forth in claim 6 wherein said step of calculating comprises calculating the concentration of the combustible gases according to the following formula:

$$I_p = 4eB(D_{O2}/(kT))[\{1 - exp(-4eV_s/(kT))\}C_{O2} - n\text{-}C_{comb}\{D_{comb}/D_{O2} - exp(-4eV_s/(kT))\}]P_T$$

8. A method of operating a selective combustible sensor, the sensor having a pump cell and a sensor cell, said method comprising the steps of:
   immersing the sensor in a gaseous atmosphere having at least two combustible gases and oxygen gas and allowing the atmosphere to enter a region between the pump cell and the sensor cell;
   applying a pumping current to the pump cell;
   sensing an electromotive force ($V_s$) across the sensor cell;
   establishing a predetermined $V_s$;
   measuring a pumping current of the pump cell; and
   calculating the concentration of the combustible gases from the measured values of the pumping current.

9. A method as set forth in claim 8 including the step of determining a $V_s$ for a zero change in pumping current with respect to a pumping current when no combustible is present for each combustible gas prior to said step of establishing.

10. A method as set forth in claim 9 wherein said step of determining comprises either one of calculating or calibrating the sensor for the zero change of each combustible gas.

11. A method as set forth in claim 8 wherein said step of establishing comprises adjusting the pumping current cell such that the sensor cell has a $V_s$ that corresponds to a zero differential pumping current for one of the combustible gases.

12. A method as set forth in claim 8 including the step of varying the temperature (T) of the sensor such that the sensor has a T that corresponds to a zero differential pumping current for one of the combustible gases prior to said step of measuring.

13. A method as set forth in claim 8 wherein said step of calculating comprises calculating the concentration of the combustible gases according to the following formula:

$$I_p = 4eB(D_{O2}/(kT))[\{1 - exp(-4eV_s/(kT))\}C_{O2} - n\text{-}C_{comb}\{D_{comb}/D_{O2} - exp(-4eV_s/(kT))\}]P_T$$

14. A method of operating a selective combustible sensor, the sensor having a pump cell and a sensor cell, said method comprising the steps of:
   immersing the sensor in a gaseous atmosphere having at least two combustible gases and oxygen gas and allowing the atmosphere to enter a region between the pump cell and the sensor cell;
   applying a pumping current to the pump cell;
   sensing an electromotive force ($V_s$) across the sensor cell;
   varying the pumping current and temperature (T) such that the sensor has a $V_s/T$ that corresponds to a zero differential pumping current for one of the combustible gases;
   measuring a pumping current of the pump cell; and
   calculating the concentration of the combustible gases from the measured values of the pumping current.

15. A method as set forth in claim 14 including the step of determining a $V_s$ for a zero change in pumping current with respect to a pumping current when no combustible is present for each combustible gas prior to said step of varying.

16. A method as set forth in claim 15 wherein said step of determining comprises either one of calculating or calibrating the sensor for the zero change of each combustible gas.

17. A method as set forth in claim 14 wherein said step of calculating comprising calculating the concentration of the combustible gases according to the following formula:

$$I_p = 4eB(D_{O2}/(kT))[\{1 - exp(-4eV_s/(kT))\}C_{O2} - n\text{-}C_{comb}\{D_{comb}/D_{O2} - exp(-4eV_s/(kT))\}]P_T$$

* * * * *